United States Patent [19]

Reader, Jr. et al.

[11] 3,970,430

[45] July 20, 1976

[54] METHOD AND APPARATUS FOR $NO_x$ ANALYSIS

[75] Inventors: John R. Reader, Jr., Middletown; James L. Seago, Wilmington; James A. Williamson, Jr., Newark, all of Del.

[73] Assignee: E. I. Du Pont de Nemours and Company, Wilmington, Del.

[22] Filed: Oct. 17, 1974

[21] Appl. No.: 515,709

[52] U.S. Cl. .......................... 23/232 R; 23/254 R; 250/373; 356/201
[51] Int. Cl.² ...................... G01N 21/24; G01J 1/42
[58] Field of Search .......... 23/232 R, 232 C, 232 E, 23/254 R, 254 E, 255 R, 255 E; 356/201, 205, 206; 250/373, 343

[56] References Cited
UNITED STATES PATENTS

| | | |
|---|---|---|
| 3,518,000 | 6/1970 | Truchelut et al. ............... 356/205 X |
| 3,654,109 | 4/1972 | Hohl et al. ......................... 250/343 |
| 3,701,601 | 10/1972 | Plumre, Jr. et al. ............. 356/201 X |
| 3,718,429 | 2/1973 | Williamson, Jr. ................. 23/232 R |
| 3,798,625 | 3/1974 | McMilliam et al. ............. 250/343 X |

*Primary Examiner*—Robert M. Reese

[57] ABSTRACT

Apparatus and method for $NO_x$ analysis in which a sample gas is introduced into a sample cell and mixed with oxygen to induce conversion of NO to $NO_2$. After a given time, prior to complete conversion of NO to $NO_2$, the absorbance and the time rate of change of absorbance is measured. The time rate of change of absorbance is indicative of the initial NO concentration in the sample gas; and the sum of the absorbance and the time rate of change of absorbance is indicative of the initial $NO_x$ concentration in the gas. A better indication of the initial $NO_x$ concentration can be obtained from the sum of the absorbance and the square root of the time rate of change of absorbance.

15 Claims, 8 Drawing Figures

METHOD AND APPARATUS FOR NOX ANALYSIS

BACKGROUND OF THE INVENTION

1. Field of the Invention

This invention relates to a photometric method and apparatus for analyzing a gas for its nitric oxide (NO) and nitrogen dioxide ($NO_2$) content. More particularly, it relates to such a method and apparatus utilizing the conversion of NO to $NO_2$ by oxygen.

2. Discussion of the Prior Art

The $NO_2$ content of a gas has previously been photometrically determined using radiation of a wavelength falling within the broad $NO_2$ absorption band. The nitrogen oxide ($NO_x$) content of such gases, however, includes not only $NO_2$ but also NO which does not absorb strongly in this wavelength band. A technique for analyzing a sample gas for its $NO_x$ content is described in U.S. Pat. No. 3,718,429, which issued on Feb. 27, 1973, to James A. Williamson, Jr. The method described in this patent proceeds by introducing the sample gas into a sample cell, introducing an oxygen-containing gas under pressure into the sample cell to bring about conversion of the NO to $NO_2$, and then detecting the $NO_x$ content by observing the increase in absorption brought about by complete conversion of NO to $NO_2$.

With normal $NO_x$ concentrations and oxygen pressures, the measurement of the $NO_x$ content of a gas by this procedure takes a relatively long period of time (on the order of 5 to 10 minutes), because the method requires complete conversion of NO to $NO_2$. Making the $NO_x$ determination over such a time period normally does not create a problem. However, if a single photometric instrument is to be used to measure the $NO_x$ content of a number of gas sources, then, the cycle time for the measurement of each gas source may reach an unacceptable level.

It has now been found that it is possible to measure the total $NO_x$ content of the gas without waiting for omplete conversion of NO to $NO_2$.

SUMMARY OF THE INVENTION

Rapid mesurement of the $NO_x$ content of a sample gas can be accomplished by measuring, at a given time, the time rate of change of absorbance of the gas and preferably the absorbance of the gas as well. The former is indicative of the initial NO concentration of the sample gas, and the sum of the two measurements is indicative of the initial $NO_x$ content of the gas. A more accurate determination can be made using the square root of the time rate of change of absorbance rather than the time rate of change of absorbance itself.

The present invention provides a method for measuring the concentration of $NO_x$ in a sample gas by
  a. introducing a known volume of the sample gas into a gas-tight sample cell;
  b. introducing at least about 2 atmospheres of an oxygen-containing gas into the cell to form a gas mixture with the sample gas;
  c. controlling the temperature and the pressure of the gas mixture in the cell;
  d. passing detecting radiation of a wavelength between about 410 to about 600 nm. through the gas mixture in the cell, the detecting radiation being of a wavelength strongly absorbed by $NO_2$; and
  e. measuring the time rate of change of absorbance of the detecting radiation by the gas mixture in the cell.

In a preferred embodiment, both the absorbance and the time rate of change of absorbance are measured at the same time; the sum of the measured absorbance and the measured time rate of change of absorbance being indicative of the initial $NO_x$ content of the sample gas.

In a still more preferred embodiment, the absorbance is summed with the square root of the time rate of change of absorbance to obtain an indication of the initial $NO_x$ concentration in the gas.

The apparatus for determining the amount of $NO_x$ in a sample gas according to the present invention comprises:
  a. a gas-tight sample cell having windows transparent to radiation of a wavelength in the range of about 410 to about 600 nm.;
  b. means for introducing a known volume of sample gas into the cell;
  c. radiation source means for passing radiation of a wavelength in the range of about 410 to about 600 nm. through the cell;
  d. detecting means for detecting the intensity of the radiation emerging from the cell;
  e. means for introducing at least about 2 atmospheres of an oxygen-containing gas into the cell to form a gas mixture with the sample gas;
  f. means for maintaining the gas mixture at a substantially constant temperature;
  g. means for maintaining the gas mixture at a substantially constant pressure; and
  h. means, connected to said detecting means, for measuring, at a given time, the time rate of change of the absorbance of radiation by the gas mixture in the cell.

A preferred apparatus further comprises means, connected to the detecting means, for measuring, at the same given time, the absorbance of radiation by the gas mixture in the cell. The sum of the measured absorbance and the measured rate of change of absorbance being indicative of the initial $NO_x$ concentration in the sample gas.

The higher oxygen pressure in the cell, the more the partial pressure of oxygen can be considered to be a constant with respect to the partial pressure of NO, so, in the preferred embodiment, the oxygen-containing gas is introduced into the sample cell at a pressure of at least about 4 atmospheres.

In a more preferred embodiment, the means for measuring the absorbance of radiation by the gas mixture in the cell is a means to generate an electrical signal proportional to the measured absorbance and the means to measure the time rate of change of absorbance or radiation by the gas mixture in the cell includes means to generate an electrical signal proportional to the square root of the measured time rate of change of absorbance. Pneumatic and fluidic signals may be generated. The apparatus also comprises means to sum the electrical signal proportional to the measure absorbance and the electrical signal proportional to the square roof of the measured time rate of change of absorbance. Means to display the output of the means to sum may also be included.

In a still more preferred embodiment, the radiation source means comprises means for passing detecting radiation through the cell, which detecting radiation is of a wavelength strongly absorbed by $NO_2$; and means for passing reference radiation through the cell, which reference radiation is of a wavelength weakly absorbed by $NO_2$. The use of reference radiation, particularly if it comes from the same source as the detecting radiation, allows one to keep a continual check on the optics of the system, and on the effect of radiation scattering by particles or mist in the sample cell. Since this reference radiation is weakly absorbed by the gas mixture, any changes in its intensity would be due to such scattering or to changes in the optical system rather than to changes in the concentration of $NO_2$ in the gas mixture.

BRIEF DESCRIPTION OF THE FIGURES

The present invention can best be described by reference to the following figures in which.

DETAILED DESCRIPTION OF THE PREFERRED EMBODIMENT OF THE INVENTION

NO is converted into $NO_2$ according to the equation:

$$2NO + O_2 \rightarrow 2NO_2.$$

The rate of reaction, $K_{ox}$, for this conversion can be written:

$$K_{ox} = [pNO]^2[pO_2],$$

where:
pNO is the partial pressure of NO in the gas mixture, and
$pO_2$ is the partial pressure of $O_2$ in the gas mixture. If the partial pressure of oxygen is large enough with respect to the partial pressure of NO, then, $pO_2$ can be considered a constant, and $$K_{ox} = [pNO]^2,$$

so that the reaction referred to above can be treated as a second order reaction. Second order reactions are described mathmetically by the following equation:

where, for this particular case:
$C_A$ = pNO at time t, and
K represents a constant.

Since the rate at which $NO_2$ is formed is equal to the rate at which NO is depleted, $$\frac{-d[pNO]}{dt} = \frac{d[pNO_2]}{dt} \; ;$$

so, substituting $$\frac{d[pNO_2]}{dt} = K[pNO]^2 \; ;$$

or $$[pNO]^2 = K' \; \frac{d[pNO_2]}{dt} \; .$$

where $K'$ is another constant.
Solution of this equation yields:

$$pNO = K'' \left( \frac{d[pNO_2]}{dt} \right)^{1/2} \; ,$$

or $$NO = K''' \left( \frac{dNO_2}{dt} \right)^{1/2} \text{ at time } t,$$

where $K''$ and $K'''$ are other constants.

For high oxygen pressure, then, the initial NO concentration can be considered to be proportional to the square root of the time rate of change of absorbance. The total $NO_x$ concentration in the sample gas, however, is equal to its NO and $NO_2$ concentration. Since the absorbance, A, of a gas is proportional to its $NO_2$ content, the total $NO_x$ concentration at a given time can be expressed as follows:

$$\text{Total } NO_x = NO_2 + K'' \left( \frac{dNO_2}{dt} \right)^{1/2} \; ; \text{ or}$$
$$\text{Total } NO_x = K_o \left[ A + K \left( \frac{dA}{dt} \right)^{1/2} \right]$$

where K and $K_o$ are constants of proportionality. By choosing the proper scale or calibration factors to account for the constants of proportionality, an absolute measure of the total $NO_x$ concentration of the gas can be obtained from a measure of the absorbance of the gas mixture and a measure of the square root of time rate of change of absorbance of the gas mixture.

The present invention utilizes detecting radiation having a wavelength of from 410 to 600 nm. to determine the concentration of $NO_2$ in a sample gas. NO is combined with an oxygen-containing gas, preferably substantially pure oxygen, under pressure in order to convert it to $NO_2$ and render it visible to the radiation.

The measurement is made before complete conversion of NO to $NO_2$ takes place. One advantage of this rapid determination of $NO_x$ concentration is that one can measure the amount of NO and $NO_2$ in the sample gas before appreciable quantities of the $NO_2$ are converted to $N_2O_4$ by a competing dimerization reaction which proceeds more slowly than the conversion of NO to $NO_2$. Controlling the temperature of the gas mixture is also significant in this respect. The basic NO to $NO_2$ reaction proceeds faster at lower temperatures, but, lower temperatures also favor the production of the invisible dimer. A temperature of 105°C. has been found to effect a compromise between these two competing reactions and allows accurate determination over a large range of concentrations. However, any temperature between about 0° and about 125°C. (preferably 50° to 125°C.) can be used.

Controlling the pressure within the sample cell also increases the accuracy of the determination because it has an effect on the amount of sample gas introduced into the cell. It may also be used to control the amount of oxygen-containing gas mixed with sample.

Reference radiation of a wavelength that is absorbed less strongly by $NO_2$ than the detecting radiation may be used to compensate for scattering by particulate matter and mist in the sample. Generally, 436 nm. and 578 nm. are preferred for the detecting and reference radiations, respectively, but other wavelengths well known to those skilled in the art of photometric determination may be used.

Figure 1:
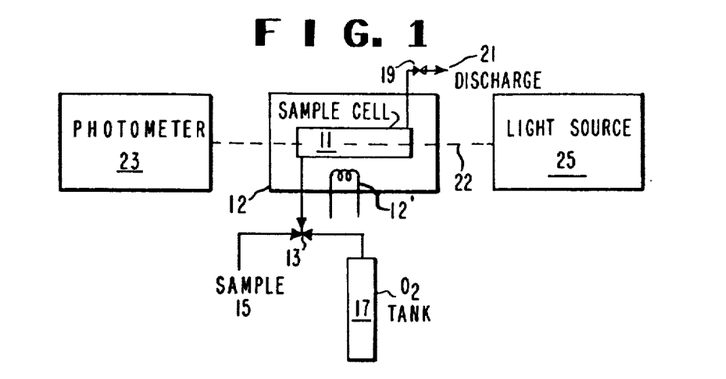
FIG. 1 is a schematic representation of the basic components of one embodiment of an apparatus used in the practice of the present invention.

FIG. 1 shows the basic components of one embodiment of an apparatus to accomplish the photometric determination of NO and $NO_2$ according to the present invention. A known volume of sample gas from sample source 15 is introduced into sample cell 11 by some suitable means. In this embodiment, the sample is passed through valve 13 into sample cell 11 which is contained within heated compartment 12. The sample may be from an auto exhaust, stack gases or any other gas source. Sample cell 11 is gas-tight and can withstand pressures of at least 2 atmospheres and preferably 5 atmospheres. Before the measurement of the $NO_x$ content, either sample gas or a purging gas can be continuously passed through the cell via valve 19 and out discharge 21. In any event, before the conversion of NO to $NO_2$, valve 19 is closed to retain a specified amount of sample within cell 11. The temperature of compartment 12, and hence call 11 and its contents, is controlled and maintained at a constant temperature by some means 12', well known to those skilled in the art. After sample gas has been introduced into the cell, an oxygen-containing gas is introduced into the sample cell by some suitable means. In this embodiment, substantially pure oxygen from $O_2$ tank 17 is introduced through valve 13 into sample cell 11, to convert NO to $NO_2$. Other oxygen-containing gases, such as air, may be used instead of pure oxygen, but substantially pure oxygen is preferred. In order to measure the $NO_2$ content of the gas, a light source 25 is provided to pass radiation 22 through sample cell 11. The transmitted radiation is detected by photometer 23. After the total $NO_x$ content of the sample gas is measured, valve 19 is opened and valve 13 positioned to pass further material for analysis from sample source 15.

Figure 2:
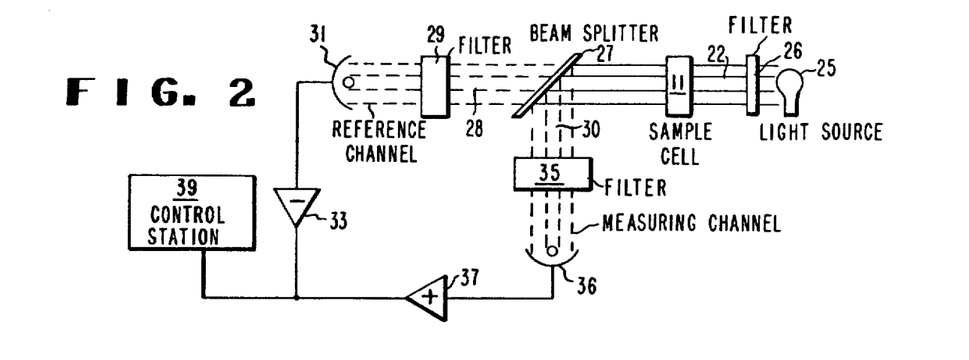
FIG. 2 shows one embodiment of a photometer which can be used in the present invention.

FIG. 2 displays one suitable photometer for use in the present invention. The radiation source means comprises means to generate detecting radiation and means to generate reference radiation. In the present embodiment, both are combined into one light source 25, which may be of any suitable type although a mercury lamp is preferred. An optical filter 26 may be provided to cut out radiation below 410 nm. from light beam 21. A Corning CS 3-73 filter is suitable. The light then passes through sample cell 11 where a portion of it is absorbed by the $NO_2$ constituent of the gas, and scattered by particulate matter and mists. After exiting cell 11, light beam 22 passes to a detecting means for detecting the intensity of the radiation emerging from the cell. In this embodiment, the radiation detecting means is a photometer 23. Upon entering the photometer, the light beam 22 is divided into two components by beam splitter 27, which in this case is a semi-transparent mirror. A portion of beam 30 passes through filter 35 which blocks all but the detecting radiation, which is responsive to both $NO_2$ absorption and scattering. Means for detecting the intensity of the detecting radiation is provided. In this embodiment, phototube 36 monitors this detecting radiation and generates an electrical signal proportional to its intensity. Its output is positively amplified by logarithmic amplifier 37. The second portion 28 of the beam from beam splitter 27 is passed through filter 29 which excluded all but reference radiation. This reference radiation responds equally to the scattering in the cell as does the measuring radiation, but is relatively less affected by $NO_2$ absorption. The reference radiation passes through filter 29 to some means to measure the intensity of the reference radiation. In this embodiment, the reference radiation is detected by phototube 31 which generates an electrical signal proportional to its intensity. The output of phototube 31 is negatively amplified by logarithmic amplifier 33. The output of negative amplifier 33 effectively subtracts the effect of scattering radiation from the output of the measuring phototube 36, thus, allowing only radiation indicative of $NO_2$ absorption to reach control station 39. This data is then available for further use.

Figure 3:
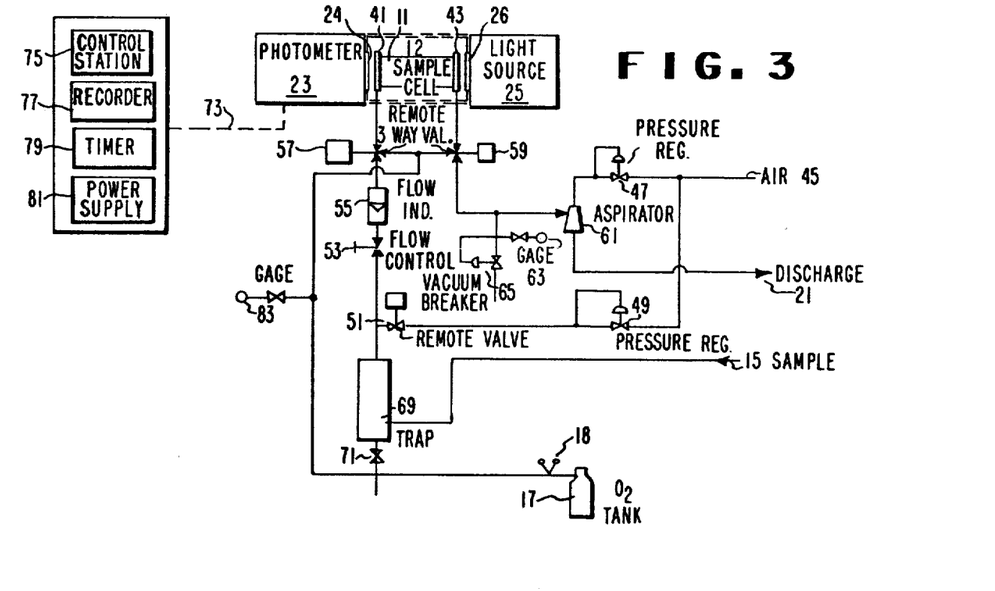
FIG. 3 shows a more detailed representation of one embodiment of the apparatus of the present invention.

FIG. 3 depicts a preferred embodiment of an apparatus according to the present invention. Photometer 23 and light source 25 are shown within windows 24 and 26, respectively. These windows are preferably quartz windows. Sample call 11 has windows 41 and 43 (also preferably by quartz) and is located within heated compratment 12. Power supply 81 powers light source 25, photometer 23, and remote valves 51, 57 and 59. Timer 79 controls the functioning of these valves. Control station 75, recorder 77, timer 79, and power supply 81 are all connected to the rest of the system by electrical interconnection 73.

Air is supplied under pressure from a source 45. This high pressure air serves two purposes. First, it continually provides gas under pressure to drive aspirator 61, which is used to create a vacuum in the line leading to the sample cell. The sample cell pressure is controlled by vacuum controller 65, and the pressure of the air supplied to aspirator 61 is regulated by pressure regulator 47. After passing through aspirator 61, the air is discharged through port 21.

The second function of the air provided from source 45 occurs during the apparatus's first cycle of operation. During this cycle, valve 51 is open and admits air under a pressure (regulated by prssure regulator 49) into the line connecting sample cell 12 to sample source 15. A portion of this air stream is used to backflush the sample line through trap 69 and cooler 67 to sample source 15. This cleanses the line in preparation for the next measurement. During this first cycle, valve 57 is opened to permit the other portion of the air stream to flow into sample cell 11, while valve 59 is open, to purge sample cell 11 and force its contents through aspirator 61 and out discharge opening 21. In this manner, the sample cell and its connections are also cleansed. Since there is no sample in cell 11 while the air is flowing through it during this first cycle, the photometer output can be zeroed by passing detecting radiation through the cell. After cell 11 and its connecting lines are cleansed, valve 51 closes and isolates the line connecting sample cell 11 and sample 15 from the air (although of course the air continues to operate aspirator 61).

The closing of valve 51 starts the second cycle of operation. During this cycle, as in the first cycle, valves 57 and 59 allow the passage of gas through valve 57 into one side of sample cell 11 and out the other side through valve 59, aspirator 61 and discharge port 21. Air from source 45, which continues to pass through aspirator 61, creates a slight vacuum in the sample cell and its connecting lines. This slight vacuum in the sample cell (without the backflushing air pressure) urges the sample gas from source 15 to flow forward through trap 69, flow control 53, flow indicator 55, valve 57, sample cell 11, valve 59, aspirator 61, and out discharge port 21. A vacuum of about 3 inches mercury at the aspirator 61 has been found to be sufficient to accomplish this. In trap 69 condensed moisture is removed. Flow indicator 55 need only be occasionally checked to ascertain that flow control 53 is permitting the correct amount of sample to flow into sample cell 11.

Vacuum breaker 65 limits and controls the magnitude of the vacuum within sample cell 11 and its connecting lines, with gauge 63 giving a visual indication of the vacuum. Vacuum breaker 65 bleeds in sufficient air to reduce the cacuum created by aspirator 61 to the desired magnitude. Because the pressure within sample cell 11 is thus accurately controlled, the amount of sample within sample cell 11 is also accurately controlled.

When a sample is within sample cell 11, value 57 then closes in order to isolate a known volume of the sample within the cell. Valve 59, however, remains open sufficiently long for the pressure (and hence the amount of sample) in sample cell 11 to be regulated and controlled by vacuum breaker 65. Then valve 59 closes and isolates the sample within sample cell 11.

During the third portion of the cycle, valves 57 and 59 both open to allow oxygen from $O_2$ tank 17 to pass through gauge 18, past gauge 83 and valves 57 and 59, into both ends of sample cell 11. Admitting the oxygen in both ends of the sample cell engenders quicker and more efficient mixing of the oxygen with the sample. Because of the general inaccuracy of double gauges such as 18 on gas tanks, gauge 83 is attached to the line in order to allow for accurate adjustment of the pressure at the oxygen tank. After the desired amount of oxygen, usually about 4 atmospheres, has been introduced into sample cell 11, valves 57 and 59 close and isolate the mixture of sample gas and oxygen within sample cell 11.

The sample gas and the oxygen within sample cell 11 are allowed to react for a given period of time. During this period, a certain amount of the NO in the sample gas is converted to $NO_2$. At a given time, the time rate of change of absorbance of the gas mixture, and preferably the absorbance as well, are measured using light source 25 and photometer 23. The details of these measurements will be described below.

After the desired measurements are made, valves 51, 57 and 59 are opened to admit air into the sample cell, its connecting lines, and the line to sample 15. This prepares the apparatus for the next determination and starts the first portion of the cycle.

With the apparatus shown in FIG. 3, and with about 0.5 to 1.5 atmospheres of sample gas, and about 4 atmospheres of oxygen in the sample cell 11, the analysis has been found to be effective for NO concentrations of from about 5 ppm. to about 10,000 ppm. of NO; although these do not represent the limits of the system. The ranges of concentration that can be detected can be changed by using different reference and detecting wave-lengths of radiation, as discussed above, and by changing the cell length. For samples having smaller concentrations of NO and $NO_2$, a longer cell length can be used.

If the conversion of NO to $NO_2$ is allowed to go to completion, the system can be used, as described in U.S. Pat. No. 3,718,429 to measure the total $NO_x$ concentrations in the sample gas. In the present invention, however, the conversion of NO to $NO_2$ is not allowed to go to completion. The measurements of absorbance and rate of change of absorbance are made at a given time, prior to complete conversion of NO to $NO_2$. The methods described below can then be used to produce a signal indicative of the total $NO_x$ concentration in the sample gas. Theoretically, the measurement of absorbance and the rate of change of absorbance of the gas mixture can be made at any time after the introduction of the oxygen into the sample cell. Practically speaking, however, time should be allowed for the system to recover from the shock of the oxygen introduction and also to allow the electronics to stabilize. Measurements made after about half a minute, preferably after a minute, yield acceptable results.

If the initial $NO_x$ concentration of a gas comprises merely NO, then the simplest way to obtain an indication of its initial $NO_x$ content is to measure its time rate of change of absorbance at a given time. One way this can be done is by plotting the absorbance and taking the slope of the plot at a given time as being indicative of the time rate of change of absorbance at that time. Alternatively, this can be instantaneously done by some means connected to the detecting means to measure the rate of change of absorbance. One way that this can be accomplished is by using a portion of the electronics shown in FIG. 4; namely, differential circuit 101. If the initial $NO_x$ concentration of the gas includes both $NO_2$ as well as NO, then one must measure both the absorbance and the rate of change of absorbance to obtain a measurement indicative of the $NO_x$ concentration. The absorbance itself is indicative of the $NO_2$ concentration in the gas, and the time rate of change of absorbance is indicative of the NO concentration in the gas.

This approach, utilizing merely the time rate of change of absorbance rather than the square root of this function, represents a first approximation to the $NO_x$ content. Its accuracy can be increased by multiplying the differential value by a scale factor, or, in the preferred situation noted below, by taking the square root of the differential value. The effectiveness of the time rate of change of absorbance approach to determining the NO concentration in a gas will be discussed in Example III. For the present, however, we will return to a discussion of the preferred operation of the present invention in which the absorbance and the square root of the time rate of change of absorbance are measured as an indication of the $NO_x$ content of the gas.

Figure 4:
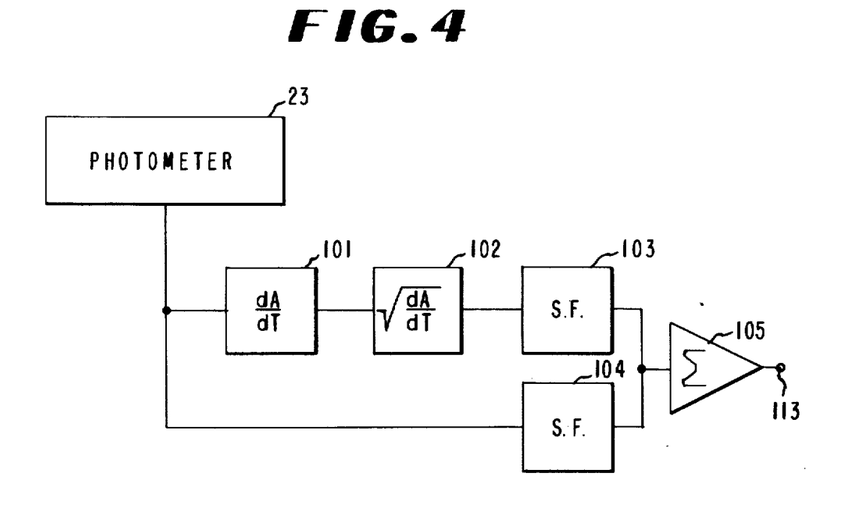
FIG. 4 shows a block diagram of one embodiment of the electronics associated with the photometer in the present invention.

As shown in FIG. 4, the output of photometer 23 is fed to a differential circuit 101 which is designed to generate a signal proportional to the time rate of change of the signal fed to it. The output of the differential circuit is in turn fed to a square root circuit 102 which is designed to generate a signal proportional to the square root of the signal fed to it. The signal from the square root circuit 102 is then fed through a scale factor circuit 103 to a summing circuit 105. The signal from the photometer is also fed to this summing circuit, through a separate scale factor circuit 104. These two signals, one of which is proportional to the absorbance of the gas mixture, and the other of which is proportional to the square root of the time rate of change of absorbance of the gas mixture, are summed. The output of this summing circuit is then displayed in some manner such as by recorder 77.

Each of the function blocks shown in FIG. 4 represent commercially available electronic circuitry. Alternatively, it is well within the skill of one of ordinary skill in the art to construct appropriate circuitry. Nevertheless, a more detailed electronic circuit diagram of one possible embodiment of the electronic shown in FIG. 4 is included as FIG. 5.

Figure 5:
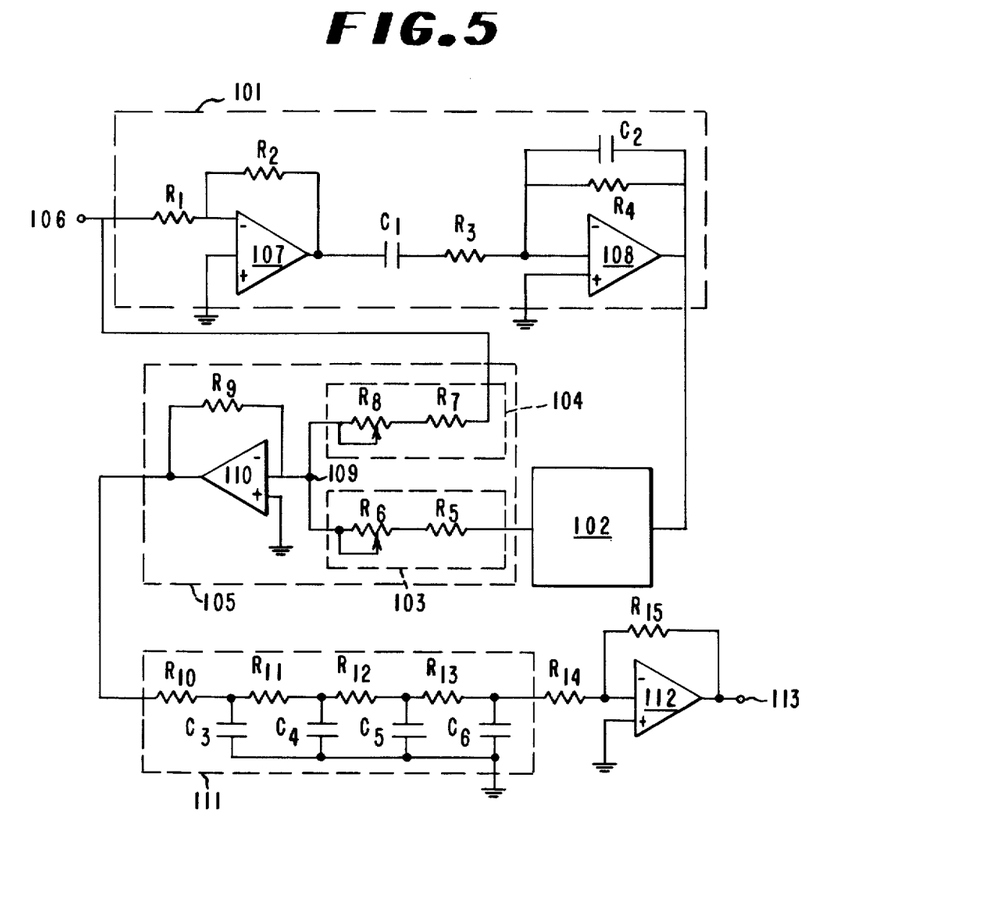
FIG. 5 is a more detailed schematic of the electronics shown in FIG. 4.

The output of photometer 23 is fed to input 106 from where it is fed directly to differential circuit 101 and scale factor circuit 104. In circuit 101, the signal is first amplified and inverted by an operational amplifier 107 and associated circuitry, and then differentiated by operational amplifier 108 and associated circuitry. The time constant is determined by the product of $C_1$ and $R_4$. $C_2$ is a roll-off capacitor to cut down on high frequency gain.

From differential circuit 101, the signal is sent to a square root circuit 102. Square root circuits are well known, and any conventional square root circuit, well known to those skilled in the art, can be used. For example, a Burr Brown 4301 circuit, sold commercially by Burr Brown, Inc., can be used as this point. The output of the square root circuit is fed to a summing circuit 105 through a scale factor circuit 103 which consists of a set resistor $R_5$ and a variable resistor $R_6$. At the same time, the output of the photometer is also fed to the summing circuit 105 through a scale factor circuit 104 which consists of a set resistor $R_7$ and a variable resistor $R_8$. The outputs of these two summing circuits are summed at a summing point 109 and then fed directly to an operational amplifier 110 and its associated resistor $R_9$. In actuality, resistors $R_5$ through $R_9$ and operational ammplifier 110 are considered to be part of the summing circuit.

The output of the summing circuit is then fed through a filter bank 111 consisting of resistors $R_{10}$ through $R_{13}$ and capacitors $C_3$ through $C_6$ which is used to smooth out high frequency oscillations of the circuits. From this filter circuit, the output is fed through an amplifier to output 113. The amplifier consists of two resistors, $R_{14}$ and $R_{15}$, and operational amplifier 112. As stated above, from output 113, the summed signal can be displayed by some means such as a recorder 77. The operational amplifiers are of conventional design, and the values of the various resistors and capacitors are shown in Table I.

TABLE I

| RESISTOR | VALUE (killohm) | RESISTOR | VALUE (killohm) | CAPACITOR | VALUE ($\mu f$) |
|---|---|---|---|---|---|
| $R_1$ | 5 | $R_9$ | 20 | $C_1$ | 1.0 |
| $R_2$ | 10 | $R_{10}$ | 37 | $C_2$ | 0.047 |
| $R_3$ | 1,000 | $R_{11}$ | 37 | $C_3$ | 27.0 |
| $R_4$ | 60,000 | $R_{12}$ | 37 | $C_4$ | 27.0 |
| $R_5$ | 4 | $R_{13}$ | 37 | $C_5$ | 27.0 |
| $R_6$ | 100 | $R_{14}$ | 4,700 | $C_6$ | 27.0 |
| $R_7$ | 4 | $R_{15}$ | 2,500 | | |
| $R_8$ | 100 | | | | |

EXAMPLE I

In this and the following examples, the analysis system shown and described with regard to FIG. 3 was used. The sample cell had an internal diameter of 2.54 cm. and a length of 50 cm. The photometer in the system was first zeroed and then a gas containing 1,000 ppm. of NO was introduced into the sample cell and allowed to run through the sample cell for one minute. After one minute, the sample inlet valve 57 was closed and five seconds later, sample outlet valve 59 was closed. Valves 57 and 59 were opened and oxygen was injected into the system at 60 pounds pressure. After about 5 seconds, both valves were again closed and oxidation of the NO to $NO_2$ was allowed to go to completion. The absorbance was measured and the recorder was set so that the recorded absorbance spanned full scale; an indication that full scale deflection constitutes 1000 parts per million of $NO_2$ in the sample gas.

The sample cell was purged and one atmosphere of gas, consisting essentially of nitrogen, containing a given amount of NO, was introduced into the sample cell. Then 4 atmospheres of oxygen were introduced into the cell. After 45 seconds, the absorbance and the rate of change of absorbance were measured. AFter 15 minutes, the rate of absorbance was measured again. The above was repeated for a number of NO concentrations and the results are shown in Table II. After 15 minutes, all of the NO in the gas is converted to $NO_2$, so "NO (15 minutes) (measured)" corresponds to the real initial value of NO in the gas; "A (45 seconds)" is the absorbance of 45 seconds given in % full scale deflection of the recorder; "dA/dt (45 seconds)" is the rate of change of absorbance at 45 seconds; "$NO_x$ (calculated)" is the calculated value of NO from the absorbance and the rate of change of absorbance; and "$\Delta$" is the difference between the real and calculated values of NO in parts per million.

$NO_x$ (calculated) is calculated from the following equation, which has already been discussed above:

TABLE II

| $NO_x$ (measured) (15 min.) | A (45 sec.) | dA/dt (45 sec.) | $dA/dt^{1/2}$ | K | $NO_x$ (calculated) | $\Delta$ |
|---|---|---|---|---|---|---|
| 992 | 74.2 | 2.58 | 1.61 | 1.55 | 1009 | −17 |
| 743 | 50.2 | 2.15 | 1.47 | 1.64 | 746 | −3 |
| 489 | 27.0 | 1.66 | 1.29 | 1.69 | 484 | +5 |
| 392 | 19.9 | 1.28 | 1.13 | 1.71 | 387 | +5 |
| 292 | 12.4 | 0.88 | 0.94 | 1.79 | 280 | +12 |
| 187 | 6.4 | 0.59 | 0.77 | 1.60 | 192 | −5 |
| 83 | 1.4 | 0.18 | 0.42 | 1.64 | 82 | +1 |
| 0 | 0 | 0 | 0 | — | 0 | |
| | | | | ave. 1.66 | | |

$$\text{Total NO}_x = K_o \left[ A + K \left( \frac{dA}{dt} \right)^{1/2} \right]$$

Since A is recorded in % full scale deflection $K_o = 10$. The value of ($K_oK$) in each case as calculated by subtracting (A × 10) from $NO_x$ (measured) (15 minutes) and dividing the differenct by $(dA/dt)^{1/2}$. The value of K for each NO concentration shown in Table II is averaged. This average value is used in the above formula to obtain the values of "$NO_x$ calculated" for each concentration.

Figure 6:
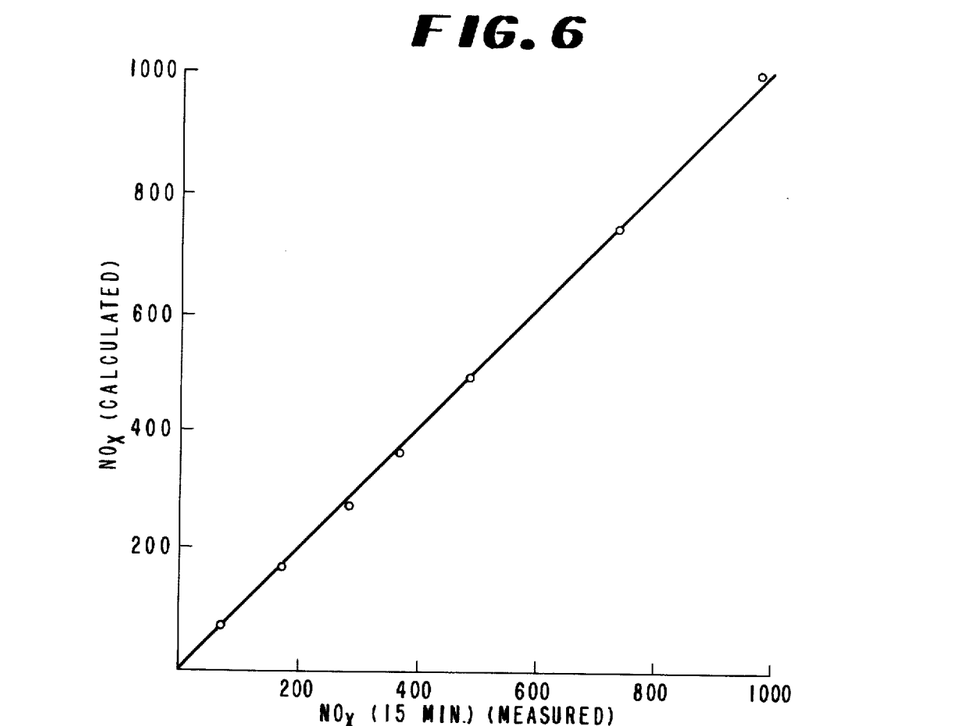
FIG. 6 is a plot of the measured $NO_x$ concentration in a gas as a function of the calculated $NO_x$ concentration.

These results are plotted in FIG. 6, In this experiment, the value of absorbance was measured from a continuous curve and the value of the time rate of change of absorbance was taken by measuring the slope of the curve at 45 seconds. The linear relation between $NO_x$ (calculated) and $NO_x$ (15 minutes) (measured) indicates the validity of the measurement.

EXAMPLE II

Figure 8:
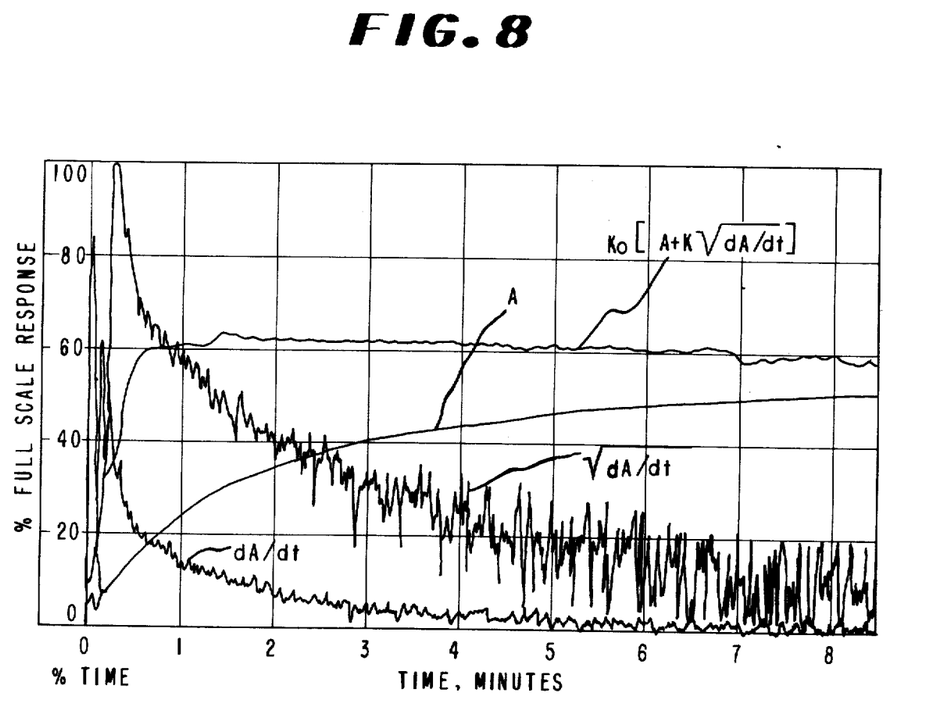
FIG. 8 is a plot of the functions generated by the electronics of FIGS. 4 and 5 as a function of time.

Using gas containing 190 parts per million of NO, and 4 atmospheres of oxygen, the above experiment was performed again. This time, however, the circuitry shown in FIG. 5 was connected between the photometer and the recorder of the system shown in FIG. 3. The results are shown in FIG. 8 where the various electronic functions are plotted in terms of percent full scale response versus the time in minutes. The exponentially increasing solid line labeled A is a plot of the absorbance as the function of time as measured by photometer 23. The wavy exponentially decreasing line labeled dA/dt is the output of the differential circuit 101 and represents the time rate of change of absorbance. The wavy decreasing line labeled $\sqrt{dA/dt}$ is the output of the square root function, and represents the square root of time rate of change of absorbance. The upper line labeled $$K_o \left[ A + K \left( \frac{dA}{dt} \right)^{1/2} \right]$$

represents the sum of the absorbance and the square root of the rate of change of absorbance and hence is indicative of the $NO_x$ concentration in the gas. The significant thing about this upper line is that, after about a minute, it is substantially flat and, therefore its value can be calibrated at any time to correspond to the absolute concentration of $NO_x$ in the sample.

EXAMPLE III

The system of Example I was zeroed and calibrated as described in Example I so that full scale deflection of the recorder indicated 1000 ppm. $NO_2$ in the sample. The sample cell was purged and a sample of gas containing a given concentration of NO was introduced into the cell. Inlet valve 57 was closed and 5 seconds later, outlet valve 59 was closed. Then both valves were opened and oxygen was introduced into the system at 60 pounds pressure. After 5 seconds, the valves were closed and two minutes after the oxygen was first introduced into the system, the absorbance was measured. Finally, 15 minutes after the oxygen was introduced into the system, the absorbance was again measured.

The deflection of the recorder 15 minutes after the oxygen was introduced into the system constitutes a measurement of the actual concentration of NO in the sample gas. This is due to the fact that complete conversion of NO to $NO_2$, will have been accomplished in this time. The value of the absorbance at two minutes after oxygen is introduced into the system constitutes a measure of the time rate of change of absorbance; in this case, the time rate of change over a two minute interval.

The same procedure was repeated using gases with varying NO concentrations. The results are shown in Table III and plotted as the solid line in FIG. 7.

TABLE III

| $NO_2$ (15 min.) | dA/dt |
|---|---|
| 66 | 2.5 |
| 78 | 3.8 |
| 88 | 4.0 |
| 125 | 5.0 |
| 480 | 35.5 |
| 750 | 63.5 |
| 1000 | 90.5 |

Figure 7:
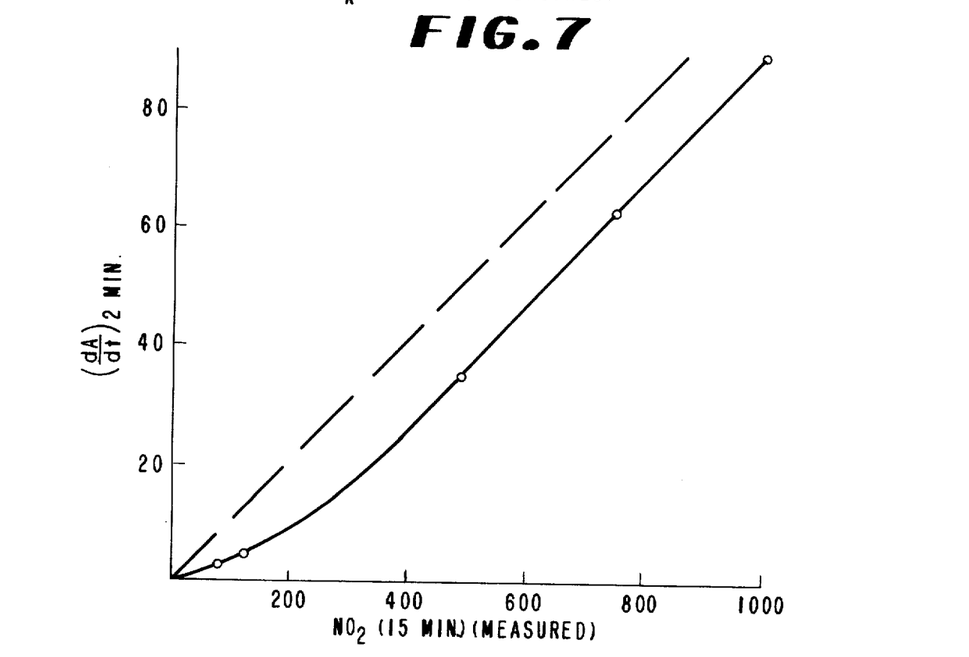
FIG. 7 is a plot of measured $dA/dt$ as a function of total NO concentration.

FIG. 7 shows that the relationship between the time rate of change of absorbance and the total initial NO concentration in the gas is a linear over most of its range; exact linearity being represented by the dashed line.

Multiplication of the time rate of change of absorbance in a scale factor in the range of from 1.1 to 1.3 will increase the linearity of the curve and its proximity to the dashed line to the point where the results obtained by this procedure are accurate to within 5% of full scale deflection. As shown in Table II, the linearity of the line can be increased still further if, instead of multiplying the rate by a scale factor, the square root of the rate is taken and multiplied by a suitable scale factor. These are two specific ways in which the basic rate approximation referred to above can be improved.

Although preferred embodiments of the invention have been described in detail as required by the patent statute, other modifications and variations within the spirit of the invention will occur to those skilled in the art, and all such modifications and variations are considered to be part of the invention described in the following claims. In particular, powers of the time rate of change substantially equivalent to the 0.5 power (i.e., about 0.4 to about 0.6) can also be used, and means to generate signals proportional to these powers can easily be built by one skilled in the art.

What is claimed is:

1. An apparatus for determining the amount of $NO_x$ in a sample gas, comprising:
   a. a gas-tight sample cell having windows transparent to radiation of a wavelength in the range of about 410 to about 600 nm.;
   b. means for introducing a known volume of sample gas into said cell;
   c. radiation source means for passing radiation of a wavelength in the range of about 410 to about 600 nm. through said cell;
   d. means for detecting the intensity of the radiation emerging from said cell;
   e. means for introducing at least about 2 atmospheres of an oxygen-containing gas into said cell to form a gas mixture with the sample gas;
   f. means for maintaining the gas mixture at a substantially constant temperature;
   g. means for maintaining the gas mixture at a substantially constant pressure;

h. means for measuring, at a given time, the time rate of change of the absorbance of radiation by the gas mixture in said cell and generating a signal proportional to the measured absorbance;
i. means for measuring, at the same time, the time rate of change of the absorbance of radiation by the gas mixture in said cell and for generating a signal proportional to the measured time rate of change of absorbance, the sum of the measured absorbance and the measured rate of change of absorbance being indicative of the initial $NO_x$ content of the sample gas; and
j. means for summing the two generated signals.

2. The apparatus of claim 1 further comprising means to multiply the time rate of change of absorbance by a scale factor between 1.1 and 1.3 and displaying the result.

3. An apparatus for determining the amount of $NO_x$ in a sample gas, comprising:
a. a gas-tight sample cell having windows transparent to radiation of a wavelength in the range of about 410 to about 500 nm.;
b. means for introducing a known volume of sample gas into said cell;
c. radiation source means for passing radiation of a wavelength in the range of about 410 to about 600 nm. through said cell;
d. means for detecting the intensity of the radiation emerging from said cell;
e. means for introducing at least about 2 atmospheres of an oxygen-containing gas into said cell to form a gas mixture with the sample gas;
f. means for maintaining the gas mixture at a substantially constant temperature;
g. means for maintaining the gas mixture at a substantially constant pressure;
h. means for measuring, at a given time, the absorbance of radiation by the gas mixture in said cell and for generating an electrical signal proportional to the measured absorbance; and
i. means for measuring, at the same time, the time rate of change of the absorbance of radiation by the gas mixture in said cell and for generating an electrical signal proportional to a power, between about 0.4 and about 0.6, of the measured time rate of change of absorbance; the sum of the measured absorbance and the power of the measured rate of chanage of absorbance being indicative of the initial $NO_x$ content of the sample gas.

4. The apparatus of claim 3 wherein said means for introducing an oxygen-containing gas into said cell comprises means for introducing at least about 4 atmospheres of substantially pure oxygen into said cell.

5. The apparatus of claim 4 wherein:
a. said means for measuring the absorbance of radiation by the gas mixture in said cell is a means to generate an electrical signal proportional to the measured absorbance; and
b. said means for measuring the time rate of change of absorbance of radiation by the gas mixture in said cell is a means to generate an electrical signal proportional to the measured time rate of change of absorbance.

6. The apparatus of claim 4 wherein said means to measure the absorbance of the gas mixture in said cell is a means to generate an electrical signal proportional to the measured absorbance; and said means for measuring the time rate of change of absorbance of radiation by the gas mixture in said cell and for generating an electrical signal proportional to a power of the measured time rate of change of absorbance is a means to generate an electrical signal proportional to the square root of the measured time rate of change of absorbance, the sum of the absorbance and the square root of the time rate of change of absorbance being indicative of the initial $NO_x$ content of the sample gas.

7. The apparatus of claim 6 further comprising:
a. means to sum the electrical signal proportional to the measured absorbance and the electrical signal proportional to the square root of the measured time rate of change of absorbance; and
b. means to display the output of said means to sum.

8. The apparatus of claim 7 wherein said radiation source means comprises:
a. means for passing detecting radiation through said cell, said detecting radiation being of a wavelength strongly absorbed by $NO_2$; and
b. means for passing reference radiation through said cell, said reference radiation being of a wavelength weakly absorbed by $NO_2$, and wherein said means for detecting the intensity of the radiation emerging from said cell comprises means for separately detecting the intensity of the detecting radiation and the reference radiation.

9. A method for measuring the concentration of $NO_x$ in a sample gas comprising the following steps:
a. introducing a known volume of the sample gas into a gas-tight sample cell;
b. introducing at least about 2 atmospheres of an oxygen-containing gas into the cell to form a gas mixture with the sample gas;
c. controlling the temperature and pressure of the gas mixture;
d. passing detecting radiation of a wavelength between about 410 to about 600 nm. through the gas mixture in the cell, said detecting radiation being of a wavelength strongly absorbed by $NO_2$; and
e. measuring, at the same given time, the absorbance and the time rate of change of absorbance of the detecting radiation passing through the cell by the gas mixture in the cell, the sum of the measured absorbance and the measured time rate of change of absorbance being indicative of the initial $NO_x$ content of the sample gas.

10. The method of claim 9 wherein, prior to the step of introducing sample gas into the cell, air is introduced into the cell and radiation of the same wavelength as said detecting radiation is passed through the air in the cell; and wherein the step of measuring the absorbance of the gas mixture is accomplished by generating an electrical signal proportional to the difference between the intensity of the detecting radiation passing through the cell when it is filled with air and the intensity of the detecting radiation passing through the cell when it is filled with sample gas.

11. The method of claim 10 wherein, in addition to detecting radiation, reference radiation is passed through the gas mixture in the cell, said reference radiation being of a wavelength weakly absorbed by $NO_2$.

12. The method of claim 11 wherein the step of measuring the absorbance and the time rate of change of absorbance of the detecting radiation passing through the gas mixture in the cell includes the step of generating an electrical signal proportional to the measured absorbance and an electrical signal proportional to the square root of the measured time rate of change of absorbance.

13. The method of claim 12 further comprising the step of summing the measured absorbance and the square root of the measured time rate of change of absorbance by generating an electrical signal proportional to the sum of measured absorbance and the square root of the measured time rate of change of absorbance.

14. The method of claim 13 further comprising the step of displaying the sum of the measured absorbance and the square root of the measured time rate of change of absorbance.

15. The method of claim 14 wherein the step of introducing an oxygen-containing gas into the cell is accomplished by introducing at least about 4 atmospheres of substantially pure oxygen into the cell.

* * * * *